United States Patent [19]

Higuchi et al.

[11] 4,430,162

[45] Feb. 7, 1984

[54] PROCESS FOR PURIFICATION OF CRUDE ACETONITRILE

[75] Inventors: Terumasa Higuchi, Yokohama; Hiroshi Susumago, Chigasaki, both of Japan

[73] Assignee: Asahi Kasei Kogyo Kabushiki Kaisha, Osaka, Japan

[21] Appl. No.: 289,628

[22] Filed: Aug. 3, 1981

Related U.S. Application Data

[62] Division of Ser. No. 131,611, Mar. 19, 1980, Pat. No. 4,308,108.

[30] Foreign Application Priority Data

Mar. 28, 1979 [JP] Japan .................................. 54-36577
Apr. 26, 1979 [JP] Japan .................................. 54-51978
Apr. 26, 1979 [JP] Japan .................................. 54-51979
May 18, 1979 [JP] Japan .................................. 54-61288

[51] Int. Cl.³ .............................................. B01D 3/34
[52] U.S. Cl. ...................................... 203/37; 203/91; 260/465.1; 260/465.3
[58] Field of Search ............... 260/465.1, 465.3, 465.9; 203/12, 14, 37, DIG. 3, 91

[56] References Cited

U.S. PATENT DOCUMENTS 4,119,497 10/1978 Ocampo et al. ...................... 203/29

Primary Examiner—Frank Sever
Attorney, Agent, or Firm—Sprung, Horn, Kramer & Woods

[57] ABSTRACT

Crude acetonitrile containing impurities such as hydrogen cyanide, allyl alcohol, oxazole and water is purified by a process including the steps of removing water lower part acetonitrile is treated with an alkali in an amount sufficient to extract water present in the crude acetonitrile, to be thereby divided into an organic liquid phase and an aqueous liquid phase, and the aqueous liquid phase is removed.

7 Claims, 6 Drawing Figures

Fig. 4
Fig. 5
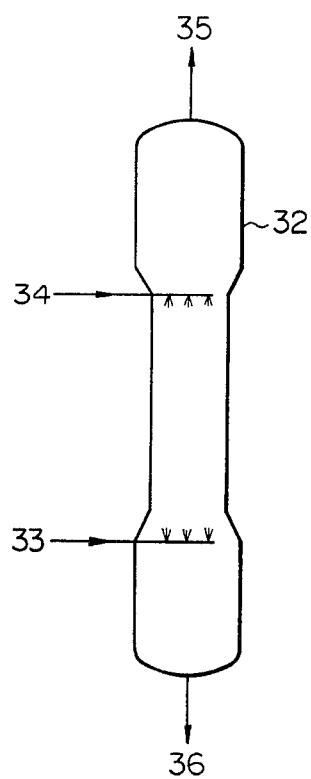
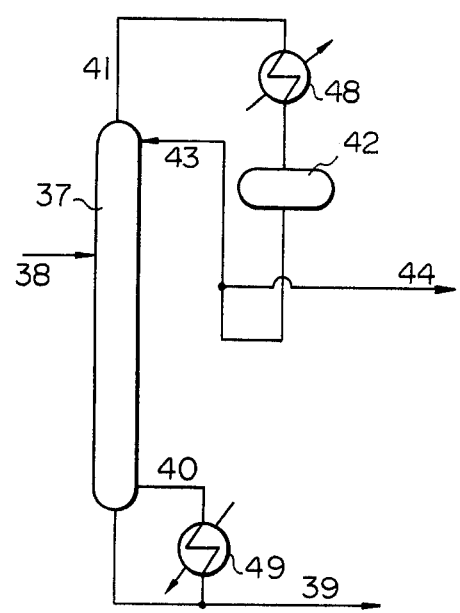

PROCESS FOR PURIFICATION OF CRUDE ACETONITRILE

This is a division of application Ser. No. 131,611, filed Mar. 19, 1980. Now U.S. Pat. No. 4,308,108.

BACKGROUND OF THE INVENTION (1) Field of the Invention

This invention relates to a process for the purification of crude acetonitrile, particularly crude acetonitrile containing impurities such as hydrogen cyanide, allyl alcohol, oxazole and water.

(2) Description of the Prior Art

Acetonitrile of the industrial grade manufactured in the petrochemical industry contains various impurities. For example, crude acetonitrile obtained as a by-product in the manufacture of acrylonitrile or methacrylonitrile by ammoxidation of propylene or isobutylene with oxygen in the presence of a catalyst is usually contaminated with impurities such as hydrogen cyanide, oxazole, water and allyl alcohol, which impurities are considered to be produced as by-products in the ammoxidation process. This crude acetonitrile obtained as a by-product in the manufacture of acrylonitrile or methacrylonitrile by ammoxidation contains acetonitrile at a low concentration and hence, cannot be used as an industrial material. That is, the above-mentioned impurities should be removed from this crude acetonitrile.

Various processes have heretofore been proposed for removing the above-mentioned impurities from crude acetonitrile. For example, there are known a process for removing hydrogen cyanide from crude acetonitrile which comprises converting both hydrogen cyanide and cyanohydrin present in the crude acetonitrile to sodium cyanide by reaction with sodium hydroxide, reacting the resulting sodium cyanide with ferrous sulfate to form sodium ferrocyanide and removing the so formed sodium ferrocyanide (see Japanese Patent Publication No. 35416/72 and Japanese Patent Publication No. 36490/70), and a process for removing hydrogen cyanide from crude acetonitrile which comprises adding an alkali to the crude acetonitrile to adjust the pH of the crude acetonitrile to from 10 to 13.5, and then, treating the crude acetonitrile with formalin in an amount of 0.5 to 2 mols per mol of the total of hydrogen cyanide and cyanohydrin present in the crude acetonitrile (see Japanese Laid-Open Patent Application Specifications No. 81816/73 and No. 25527/75). However, since the former process needs both the alkali treatment and the ferrous sulfate treatment, the steps of the process become complicated and the equipment costs and labor expenses are inevitably increased. Furthermore, since these treatments must be conducted at a high temperature, and already once recovered acetonitrile is readily hydrolyzed and the recovery ratio of acetonitrile is reduced. The latter process involves many steps, and the equipment costs and labor expenses are increased, and if an alkali is added in an amount larger than the equimolar amount to the sum of the hydrogen cyanide and cyanohydrin, decomposition of cyanohydrin takes place and also hydrolysis of acetonitrile is readily caused.

Removal of allyl alcohol contained in crude acetonitrile by rectification is very difficult because the boiling point of allyl alcohol is very close to the boiling point of acetonitrile. As means for removing allyl alcohol from crude acetonitrile, there are known a process comprising adding a hypochlorite and a mineral acid to crude acetonitrile and subjecting the mixture to distillation (see Japanese Patent Publication No. 4531/77), a process comprising adding hydrogen chloride to crude acetonitrile to convert allyl alcohol to allyl chloride and separating the so formed allyl chloride by distillation (see Japanese Laid-Open Patent Application Specification No. 156815/77), and a process comprising adding sulfuric acid to crude acetonitrile and subjecting the reaction mixture to distillation (see Japanese Laid-Open Patent Application Specification No. 23218/76).

In these treatment processes using additive chemicals, since equipments used are readily corroded by these chemicals, it is necessary to use equipment and apparatuses constructed of special materials. Furthermore, special care must be paid to the treatment of waste waters from these processes. Accordingly, it has been eagerly desired in the art to develop a process for removing allyl alcohol from crude acetonitrile by a simple operation without addition of a chemical.

As the process for dehydration purification of crude wet acetonitrile, there are known an extraction dehydration process using calcium chloride and an extraction distillation process using benzene (see U.S. Pat. No. 3,451,899 and Japanese Patent Publication No. 36490/70). However, when organic compound-containing waste water discharged from the extraction step in the former process is treated according to conventional waste water treatment procedures under high temperature and high pressure conditions, the treatment apparatus is readily corroded by chlorine ions present in the waste water, and therefore, special considerations must be taken in the waste water treatment. In the latter process, since water is separated in the form of steam, a large quantity of heat is necessary, and benzene is wastefully consumed because it readily escapes from the extraction distillation system.

Complete removal of oxazole from crude acetonitrile by rectification is very difficult because the boiling point of oxazole is also very close to that of acetonitrile. As means for removing oxazole contained in crude acetonitrile, there is known a process comprising adding a specific inorganic salt to crude acetonitrile to form an oxazole-inorganic salt complex compound, precipitating the complex compound and removing the precipitated complex compound (see British Patent No. 1,156,713). In this process, a special chemical must be used and a very troublesome operation is necessary for the separation of the formed precipitate.

As the process for the purification of crude acetonitrile containing hydrogen cyanide, acrylonitrile and water, U.S. Pat. No. 4,119,497 (patented Oct. 10, 1978) proposes a process comprising adding a base selected from alkali metal hydroxides, ammonium hydroxide, ammonia and aliphatic amines to the crude acetonitrile to convert hydrogen cyanide and acrylonitrile to organic compounds of higher molecular weight, removing water in the form of an azeotropic mixture with benzene in a subsequent azeotropic distillation column and separating the compounds of higher molecular weight in a final rectifying column to recover purified acetonitrile. This process is characterized in that hydrogen cyanide is converted to higher molecular weight compounds according to the following reactions and is removed in the form of these higher molecular weight compounds:

$$HCN + 2H_2O \xrightarrow{NaOH} H-COONH_2$$

$$H-COONH + NaOH \longrightarrow H-COONa + NH_4OH$$

$$HCN + 2H_2O \xrightarrow{NH_4OH} H-COONH_2$$

The rate of these reactions is slow and thus, it is necessary to use excessive amounts of the bases to complete the above reactions within a reasonably short period of time. Furthermore, when unsaturated nitriles, such as acrylonitrile, are contained as impurities, it is necessary to add the bases in great excess to the crude acetonitrile irrespective of the content of hydrogen cyanide in the crude acetonitrile. This is not preferred because decomposition of acetonitrile is caused.

Hydrogen cyanide contained in crude acetonitrile separated from the reaction product obtained by ammoxidation of propylene or isobutylene is ordinarily present in the form of combined hydrogen cyanide such as cyanohydrin, for example, acetone cyanohydrin. Such cyanohydrin is ordinarily very unstable and separation thereof according to the above process is very difficult. Especially, when the crude acetonitrile contains hydrogen cyanide at a high concentration, a higher temperature and a longer reaction time are necessary for completion of the above chemical reactions, and in this case, decomposition of acetonitrile readily occurs, resulting in reduction of the recovery ratio of acetonitrile.

According to the above process, water is removed by extractive distillation using benzene, and as in the above-mentioned processes proposed in U.S. Pat. No. 3,451,899 and Japanese Patent Publication No. 36490/70, problems of wasteful consumption of benzene arise, owing to the escape of benzene from the distillation system and the mingling of benzene into the purified product. Furthermore, allyl alcohol and oxazole, contained as impurities in crude acetonitrile obtained in the process of ammoxidation of propylene or isobutylene, cannot completely be removed according to this process.

SUMMARY OF THE INVENTION

It is, therefore, an object of the present invention to provide a process for removing hydrogen cyanide from crude acetonitrile containing hydrogen cyanide as a major impurity component by treating the crude acetonitrile with an alkali, in which hydrogen cyanide can be effectively removed at a high efficiency by a simple operation while reducing the amount of the alkali used to a level as low as possible and controlling the decomposition of cyanohydrin, sodium cyanide and acetonitrile.

Another object of the present invention is to provide a process for removing allyl alcohol from crude acetonitrile containing allyl alcohol as a major impurity componet, in which allyl alcohl can be effectively removed without the addition of any particular chemical.

Still another object of the present invention to provide a process for removing water from crude acetonitrile containing water as a major impurity component, in which water can be effectively removed by extraction using an alkali.

A further object of the present invention is to provide a process for removing oxazol from crude acetonitrile containing oxazole as a major impurity component, in which oxazole can be effectively removed without the addition of any particular chemical.

A still further object of the present invention is to provide a process for removing hydrogen cyanide and allyl alcohol from crude acetonitrile containing hydrogen cyanide and allyl alcohol as major impurity components, in which these impurity components can be effectively removed at a high efficiency by a simple operation.

A still further object of the present invention is to provide a process for removing oxazole and water from crude acetonitrile containing oxazole and water as major impurity components, in which these impurity components can be effectively separated at a high efficiency.

A still further object of the present invention is to provide a process for removing hydrogen cyanide, allyl alcohol, oxazole and water from crude acetonitrile containing hydrogen cyanide, allyl alcohol, oxazole and water as major impurity components, in which these impurity components can be effectively separated at a high efficiency.

In accordance with the present invention, crude acetonitrile, containing as a major impurity component at least one compound selected from hydrogen cyanide, allyl alcohol, water and oxazole, is purified according to the following processes.

Crude acetonitrile containing hydrogen cyanide as a major impurity component is purified by treating the crude acetonitrile with an alkali in an amount sufficient to convert a substantial part of the free hydrogen cyanide present in the crude acetonitrile to an alkali metal cyanide but insufficient to convert a substantial part of the combined hydrogen cyanide present in the crude acetonitrile to an alkali metal cyanide; and then, subjecting the reaction mixture to distillation under reduced pressure.

Crude acetonitrile containing allyl alcohol as a major impurity component is purified by subjecting the crude acetonitrile to extractive distillation in the presence of water in a rectifying column, while acetonitrile together with a small amount of water is recovered from the upper part of the column, and a concentrate of allyl alcohol in the form of a mixture with water and a small amount of acetonirtile is separated from the lower part of the column.

Crude acetonitrile containing oxazole as a major impurity component is purified by subjecting the crude acetonitrile to extractive distillation in the presence of 0.5 to 5% by weight of water in a rectifying column, while a concentrate of oxazole in the form of a mixture with water and a small amount of acetonitrile is separated from the upper part of the column, and acetonitrile is recovered from the lower part of the column.

Crude acetonitrile containing water as a major impurity component is purified by treating the crude aqueous acetonitrile with an alkali in an amount sufficient to extract water present in the crude aqueous acetonitrile, to divide the crude aqueous acetonitrile into an organic liquid phase and an aqueous liquid phase, and removing the aqueous liquid phase.

Crude acetonitrile containing hydrogen cyanide and allyl alcohol as major impurity components is purified by treating the crude acetonitrile with an alkali in an amount sufficient to convert a substantial part of the free hydrogen cyanide present in the crude acetonitrile to an alkali metal cyanide but insufficient to convert a substantial part of the combined hydrogen cyanide present in the crude acetonitrile to an alkali cyanide; and then, subjecting the reaction mixture to distillation under reduced pressure in a rectifying column.

Crude acetonitrile containing oxazole and water as major impurity components is purified by treating the crude aqueous acetonitrile with an alkali in an amount sufficient to extract water contained in the crude aqueous acetonitrile to divide the crude aqueous acetonitrile into an organic liquid phase and an aqueous liquid phase; removing the aqueous liquid phase; and then, subjecting the residual organic liquid phase to extractive distillation in the presence of 0.5 to 5% by weight of water in a rectifying column, while a concentrate of oxazole in the form of a mixture with water and a small amount of acetonitrile is separated from the upper part of the column, and acetonitrile is recovered from the lower part of the column.

Crude acetonitrile containing hydrogen cyanide, allyl alcohol, oxazole and water as main impurity components is purified by treating the crude aqueous acetonitrile with an alkali in an amount sufficient to convert a substantial part of the free hydrogen cyanide present in the crude acetonitrile to an alkali metal cyanide but insufficient to convert a substantial part of the combined hydrogen cyanide present in the crude aqueous acetonitrile to an alkali metal cyanide; subjecting the reaction mixture to distillation under reduced pressure in the presence of water in a rectifying column, to separate hydrogen cyanide and allyl alcohol from the crude acetonitrile; treating the residual crude acetonitrile with an alkali in an amount sufficient to extract water present in the residual crude acetonitrile to divide the residual crude acetonitrile into an organic liquid phase and an aqueous liquid phase; and then, removing the aqueous layer, and subjecting the organic liquid phase to extractive distillation in the presence of 0.5 to 5% by weight of water in a rectifying column, while a concentrate of oxazole in the form of a mixture with water and small amount of acetonitrile is separated from the upper part of the column, and acetonitrile is recovered from the lower part of the column.

BRIEF DESCRIPTION OF THE DRAWINGS

FIG. 4 is a diagram illustrating one embodiment of the apparatus for separating water from crude acetonitrile containing water;

FIG. 5 is a flow sheet illustrating one embodiment of the process for separating oxazole from crude acetonitrile containing oxazole; and, FIG. 6 is a flow sheet illustrated one embodiment of the process for separating hydrogen cyanide, allyl alcohol, water and oxazole from crude acetonitrile containing hydrogen cyanide, allyl alcohol, water and oxazole.

DETAILED DESCRIPTION OF THE PREFERRED EMBODIMENTS

Figure 1:
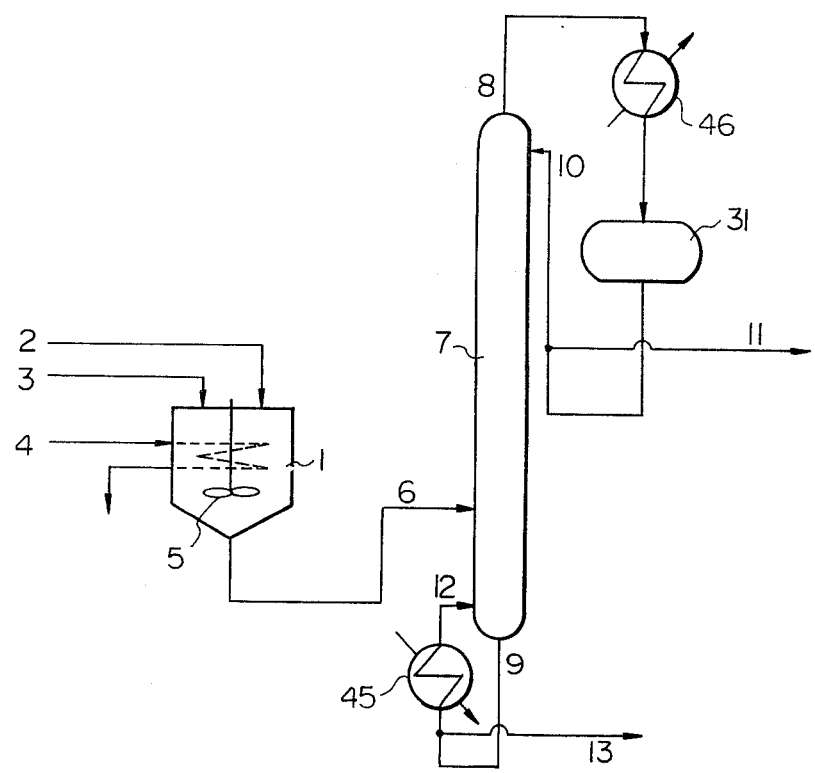
FIG. 1 is a flow sheet illustrating one embodiment of the process for separating hydrogen cyanide from crude acetonitrile containing hydrogen cyanide.

Processes for the purification of crude acetonitrile according to the present invention will now be described in detail.

The crude acetonitrile to be purified contains at least one impurity component selected from hydrogen cyanide (i.e., free hydrogen cyanide and combined hydrogen cyanide such as cyanohydrins), allyl alcohol, oxazole and water. A typical instance of the crude acetonitrile is crude acetonitrile obtained as a by-product in the manufacture of acrylonitrile or methacrylonitrile by ammoxidation of propylene or isobutylene, which acetonitrile usually comprises the following components.

| Component | Content (% by weight) |
|---|---|
| Acetonitrile | 15–70 |
| Water | 20–70 |
| Free hydrogen cyanide | 0.1–10 |
| Cyanohydrin type hydrogen cyanide | 0.1–5 |
| Acetone | 0.1–3 |
| Acrylonitrile | 0.1–3 |
| Propionitrile | 0.5–3 |
| Allyl alcohol | 0.1–2 |
| Oxazole | 0.1–3 |
| Ammonia | 0.1–3 |
| Unknown components | 0.1–5 |

For convenience's sake, the present invention will be described successively according to the kinds of major impurity components present in crude acetonitrile.

(i) Purification of Crude Acetonitrile Containing Hydrogen Cyanide:

An alkali is added to crude acetonitrile containing hydrogen cyanide in an amount sufficient to convert a substantial part of the free hydrogen cyanide present in the crude acetonitrile to an alkali cyanide but insufficient to convert a substantial part of the combined hydrogen cyanide present in the crude acetonitrile to an alkali cyanide, preferably in an amount of 1 to 3 mols per mol of the free hydrogen cyanide, thereby to effect reaction between the alkali and the hydrogen cyanide and, then, subjecting the reaction mixture to distillation under reduced pressure, preferably at a temperature of not higher than approximately 70° C.

A typical instance of the crude acetonitrile containing hydrogen cyanide as a main component is crude acetonitrile obtained in the process for manufacturing acrylonitrile or methyacrylonitrile by ammoxidation. However, other crude acetonitrile can also be purified in the above-mentioned process, provided that the crude acetonitrile contains less than 10% by weight of free hydrogen cyanide and less than 7% by weight of combined hydrogen cyanide.

An aqueous solution of sodium hydroxide or potassium hydroxide is preferably employed as the alkali. This embodiment of the present invention is different from the conventional process using an alkali in the point where the amount of the alkali used in the process of the present invention is such that the alkali reacts with a substantial part of the free hydrogen but does not react with the cyanohydrin type hydrogen cyanide cyanohydrin. Ordinarily, this amount is selected within the range of from 1.0 to 3.0 mols per mol of the free hydrogen cyanide present in the crude acetonitrile. If the amount of the alkali is smaller than 1 mol per mol of free hydrogen cyanide, hydrogen cyanide cannot be completely removed, and, in contrast, if the amount of the alkali is larger than 3 mols per mol of free hydrogen cyanide, no good results are obtained because acetonitrile is hydrolyzed.

This alkali treatment is preferably carried out at a temperature of 20° to 80° C., more preferably 50° to 75° C., for 0.5 to 10 hours, preferably 5 to 6 hours. If desired, the alkali treatment may be conducted with stirring.

The reaction mixture obtained by the alkali treatment is subjected to distillation at a temperature as low as possible in order to control decomposition of hydrogen cyanide of the cyanohydrin type or the alkali cyanide.

For this purpose, distillation is carried out under reduced pressure so as to lower the boiling point of the reaction mixture. More specifically, distillation is preferably conducted at a temperature not exceeding 70° C., particularly 30° to 60° C., under a pressure of 50 to 400 Torr, particularly 80 to 200 Torr.

By the above treatments, not only free hydrogen cyanide but also hydrogen cyanide of the cyanohydrin type, contained in crude acetonitrile, can be removed substantially completely, and at the same time, acetonitrile is concentrated.

(ii) Purification of Crude Acetonitrile Containing Allyl Alcohol:

Crude acetonitrile containing allyl alcohol is subjected to extractive distillation in the presence of water in a rectifying column, while acetonitrile is recovered together with a small amount of water from the upper part of the column and concurrently therewith a concentrate of allyl alcohol in the form of a mixture with water and a small amount of acetonitrile is separated from the lower part of the column.

A typical instance of the crude acetonitrile containing allyl alcohol as a main impurity component is crude acetonitrile obtained in the process for manufacturing acrylonitrile or methacrylonitrile by ammoxidation of propylene or isobutylene. However, other crude acetonitrile can also be purified by the above-mentioned process, provided that the crude acetonitrile contains from 5 ppm to 10% by weight of allyl alcohol.

In the case where the crude acetonitrile contains a relatively large amount, e.g., from 25% to 70% by weight, of water, it is not particularly necessary to add water for the extractive distillation, but the crude acetonitrile is fed to the distillation step as it is. At the extractive distillation operation, the crude acetonitrile and water are fed to the intermediate part of the rectifying column independently or in the form of a preformed mixture. Acetonitrile is recovered from the upper part of the column in the form of an azeotropic mixture with water or a mixture having a composition very close to the azeotropic mixture, while a concentrate of allyl alcohol in the form of a mixture with water and a small amount of acetonitrile is separated from the lower part of the column. This process is conducted preferably in a continuous manner.

Under the conditions of this process, the relative volatility of acetonitrile to allyl alcohol is remarkably increased, and distillation separation of allyl alcohol from acetonitrile becomes possible. This is in contrast to the conventional distillation process wherein allyl alcohol cannot completely be separated from acetonitrile.

The efficiency of separation of allyl alcohol and the efficiency of recovery of acetonitrile are influenced by the amount of water present in the distillation system.

More specifically, in the case where the amount of water present in the distillation system is a stoichiometric amount for formation of an azeotropic mixture of water and acetonitrile and an azeotropic mixture of allyl alcohol and water, or an amount close to this stoichiometric amount, the efficiency of separation of allyl alcohol is increased and the recovery ratio of acetonitrile is highly improved. In contrast, if the amount of water present in the distillation system is smaller than the above-mentioned amount necessary for formation of the azeotropic mixtures, the efficiency of separation of allyl alcohol is reduced and therefore, the recovery of purified acetonitrile is reduced. If the amount of water present in the distillation system is much larger than the stoichiometric amount providing azeotropic compositions, i.e., the amount of water exceeds 1.5 times of the stoichiometric amount, the efficiency of separation of allyl alcohol is lowered and therefore, the recovery of purified acetonitrile is reduced.

The distillation may be carried out under atmospheric pressure, but in order to separate allyl alcohol efficiently and recover purified acetonitrile at a high recovery ratio, it is convenient to conduct the extraction operation under a reduced pressure of 50 to 760 Torr, preferably 80 to 400 Torr, more preferably 100 to 200 Torr.

(iii) Purification of Water-Containing Crude Acetonitrile:

An alkali is incorporated in and mixed with crude acetonitrile in an amount sufficient to extract water present in the crude acetonitrile, and the formed aqueous liquid phase is removed.

According to the conventional process, an extracting agent which does not cause hydrolysis of acetonitile, such as benzene or calcium chloride, is used. It has been unexpectedly found that according to the present invention, crude wet acetonitrile can be efficiently purified by using an alkali which is ordinarily considered to readily cause hydrolysis of acetonitrile.

A typical instance of the crude aqueous acetonitrile to be purified in this embodiment is crude acetonitrile obtained in the process for manufacturing acrylonitrile or methacrylonitrile by ammoxidation. However, other crude acetonitrile can also be purified in this embodiment if the content of water in the crude acetonitrile is in the range of from 5 to 85% by weight.

Both a solid alkali and an aqueous alkali solution can be used as the agent for extracting water. However, an aqueous solution containing from about 30% to about 50% by weight of sodium hydroxide or sodium hydroxide is preferable.

This purification process may be carried out at a temperature of 10° to 50° C., preferably 20° to 30° C. If the temperature is higher than 50° C., acetonitrile is readily hydrolyzed, and if the temperature is lower than 10° C., the viscosity of the crude acetonitrile is increased and the adaptability of the crude acetonitrile to the operation is reduced. The amount of the alkali used varies depending upon the water content in the crude acetonitrile or the desired water content in purified acetonitrile, but ordinarily, the amount of the alkali used is selected within the range of 10 to 50% by weight based on water contained in the crude acetonitrile.

According to this embodiment, acetonitrile having a water content of 1 to 3% by weight can easily be obtained, and if desired, purified acetonitrile having a lower water content can be recovered. The aqueous liquid phase separated from acetonitrile in this embodiment may contain hydrogen cyanide, acrylonitrile and other impurities in addition to the alkali and water. This aqueous liquid phase can be utilized as an alkali source in the acetonitrile purification process as disclosed in, for example, Japanese Patent Publication No. 35416/72 and Japanese Laid-Open Patent Application Specification No. 81816/73. If this procedure is adopted, acetonitrile, which will otherwise be discarded in the state contained in the waste alkali solution, can be supplied to the other acetonitrile purification process, and therefore, the overall recovery ratio of acetonitrile can be increased.

(iv) Purification of Crude Acetonitrile Containing Oxazole:

Crude acetonitrile containing oxazole is subjected to extractive distillation in the presence of water in a rectifying column, while a concentrate of oxazole in the form of a mixture with water and a small amount of acetonitrile is separated from the upper part of the column and acetonitrile is recovered from the lower part of the column.

A typical instance of the crude acetonitrile containing oxazole as a main impurity component is crude acetonitrile obtained in the process for manufacturing acrylonitrile or methacrylonitrile by ammoxidation of propylene or isobutylene.

The crude acetonitrile to be purified may contain water, ammonia, acetone, acrylonitrile and other low-boiling-point compounds in addition to oxazole, and these impurities can also be removed together with oxazole in this embodiment. Usually, crude acetonitrile containing from 100 ppm to 20% by weight of oxazole can be purified in this embodiment.

The crude acetonitrile and water are fed to the intermediate part of the rectifying column independently or in the form of a preformed mixture, and they are subjected to distillation. It is preferred that the amount of water in the crude acetonitrile be adjusted to 0.5 to 5% by weight. If the amount of water is controlled within this preferred range, the amount of water present in the vicinity of the crude acetonitrile feeding inlet is 0.5 to 5% by weight and optimum operation conditions can be obtained. In order to save the quantity of the vapor used for distillation and improve the recovery ratio of acetonitrile, it is especially preferred that the amount of water in the crude acetonitrile be adjusted to 1 to 3% by weight. When the water content in the crude acetonitrile exceeds this range, good results are obtained by dehydrating the starting crude acetonitrile in advance. The crude acetonitrile and water are fed into the rectifying column preferably at a height about $\frac{1}{2}$ to about $\frac{3}{4}$ of the total column height, especially about $\frac{2}{3}$ of the total column height, from the column bottom.

By this extractive distillation, a concentrate of oxazole in the form of a mixture with 5 to 20% by weight of water and a small amount of acetonitrile is separated from the upper part of the column, and acetonitrile free of oxazole is recovered from the lower part of the column. Under the conditions of this embodiment, the relative volatility of oxazole to acetonitrile is remarkably increased, and therefore, distillation separation of oxazole from acetonitrile becomes possible, though complete separation of oxazole from acetonitrile by distillation is impossible according to the conventional distillation process. By this distillation separation, low-boiling-point impurities are removed from the upper part of the column in the form of vapors, and purified acetonitrile is recovered at a recovery of higher than 90%. This process may be conducted in a continuous or batchwise manner.

The distillation column to be used in this embodiment is not particularly critical, but ordinarily, a perforated plate type distillation column including 20 to 60 plates is used. As the distillation conditions, there are selected a column bottom pressure of 0.1 to 0.3 kg/cm$^2$ (all of the pressures expressed in terms of the unit "kg/cm$^2$" in this specification refer to the gauge pressure), a column bottom temperature of 85° to 95° C., a column top pressure of 0.01 to 0.03 kg/cm$^2$ and a column top temperature of 75° to 85° C.

(v) Purification of Crude Acetonitrile Containing Hydrogen Cyanide and Allyl Alcohol:

An alkali is added to this crude acetonitrile containing hydrogen cyanide and allyl alcohol, in an amount sufficient to convert free hydrogen cyanide present in the crude acetonitrile to an alkali cyanide, and the resulting crude acetonitrile containing the alkali cyanide and allyl alcohol is subjected to extractive distillation in the presence of water in a rectifying column while acetonitrile is recovered together with a small amount of water from the upper part of the column.

Under the conditions adopted in this embodiment, the relative volatility of acetonitrile to allyl alcohol and hydrogen cyanide (alkali cyanide) is remarkably increased, and complete separation of allyl alcohol and hydrogen cyanide from acetonitrile, which has been impossible according to the conventional distillation process, can be attained very effectively and allyl alcohol and hydrogen cyanide can be simultaneously separated from acetonitrile very easily. Either free hydrogen cyanide or cyanohydrin type hydrogen cyanide can be removed substantially completely and at the same time, acetonitrile is concentrated.

A typical instance of the crude acetonitrile of this type to be purified is crude acetonitrile obtained in the process for manufacturing acrylonitrile or methacrylonitrile by ammoxidation. However, other crude acetonitrile can also be purified in this embodiment provided that the contents of free hydrogen cyanide, combined hydrogen cyanide and allyl alcohol in the crude acetonitrile are less than 10% by weight, less than 7% by weight and from 5 ppm to 10% by weight, respectively.

The kind and amount of the alkali to be used and the alkali treatment conditions may be the same as described in (i) above.

The reaction mixture formed by the alkali treatment is then subjected to extractive distillation in the presence of water in a rectifying column. In order to control decomposition of hydrogen cyanide of the cyanohydrin type or the alkali cyanide, the distillation is carried out under a reduced pressure at a temperature as low as possible. More specifically, distillation conditions of a distillation temperature not exceeding 70° C., particularly 30° to 60° C., and a distillation pressure of 50 to 400 Torr, particularly 80 to 200 Torr, are preferably adopted.

This extraction distillation is preferably conducted in the following manner. The crude acetonitrile and water are supplied to the intermediate part of the rectifying column independently or in the form of a preformed mixture, and an azotropic mixture of acetonitrile and water or a mixture having a composition close to the azeotropic composition is continuously recovered from the upper part of the column while a mixture comprising allyl alcohol, alkali cyanide, cyanohydrin, water and a small amount of acetonitrile is continuously separated from the bottom of the column.

As pointed out in (ii) above, the efficiency of separation of allyl alcohol and the recovery ratio of acetonitrile are remarkably influenced by the amount of water made present in the distillation system, and the amount of water may be appropriately decided according to the composition of the crude acetonitrile and the intended used of the purified acetonitrile.

(vi) Purification of Crude Acetonitrile Containing Oxazole and Water:

This purification process comprises the above-mentioned processes (iii) and (iv) in combination. More specifically, an alkali is added to this crude acetonitrile containing oxazole and water in an amount sufficient to extract water present in the crude acetonitrile, and the crude acetonitrile is mixed. The separated aqueous liquid phase is removed and the crude acetonitrile containing 0.5 to 5% by weight of water is recovered. The so recovered crude acetonitrile is then subjected to extractive distillation in a rectifying column, while a concentrate of oxazole in the form of an aqueous mixture containing a small amount of acetonitrile is separated from the upper part of the column and acetonitrile free of water or oxazole is recovered from the lower part of the column. Under the conditions of this embodiment, the relative volatility of oxazole to acetonitrile is remarkably increased, and therefore, oxazole and water can easily be separated from acetonitrile simultaneously, although these impurities cannot completely be separated from acetonitrile according to the conventional distillation process.

A typical instance of the crude acetonitrile of this type is crude acetonitrile obtained in the process for manufacturing acrylonitrile or methacrylonitrile by ammoxidation. However, other crude acetonitrile can also be purified in this embodiment, provided that the contents of oxazole and water in the crude acetonitrile are from 100 ppm to 20% by weight and from 5 to 85% by weight, respectively.

The kind of the alkali to be used as the water extracting agent and the alkali treatment temperature may be the same as described in (iii) above. The alkali is added in an amount necessary to reduce the water content in the purified acetonitrile to 0.5 to 5% by weight. Ordinarily, this amount corresponds to 10 to 50% by weight based on water contained in the crude acetonitrile.

The aqueous liquid phase separated from the acetonitrile phase can be utilized as an alkali supply source in the purification of acetonitrile as described in (iii) above.

The crude acetonitrile, from which water has been removed by the alkali treatment, is then supplied to the rectifying column from the upper part thereof in the state containing 0.5 to 5% by weight of water and is subjected to extractive distillation. A concentrate of oxazole in the form of a mixture with 5 to 20% by weight of water and a small amount of acetonitrile is separated from the upper part of the column while acetonitrile free of oxazole or water is recovered from the lower part of the column. The water content in the crude acetonitrile to be supplied to the rectifying colum is adjusted as described in (iv) above, and the dimensions of the distillation column and the distillation conditions may be the same as described in (iv) above.

(vii) Purification of Crude Acetonitrile Containing Hydrogen Cyanide, Allyl Alcohol, Oxazole and Water:

This purification process comprises the above-mentioned processes (v) and (vi) in combination. More specifically, an alkali is added to this crude acetonitrile containing hydrogen cyanide, allyl alcohol, oxazole and water, in an amount sufficient to convert a substantial part of the free hydrogen cyanide present in the crude acetonitrile to an alkali cyanide but insufficient to convert a substantial part of the combined hydrogen cyanide present in the crude acetonitrile to an alkali cyanide, and the mixture is reacted to effect this conversion. The reaction mixture is subjected to distillation under reduced pressure in the presence of water in a rectifying column, while alkali cyanide, cyanohydrin-type hydrogen cyanide and allyl alcohol are separated from the crude acetonitrile. Then, an alkali is added to the residual crude acetonitrile in an amount sufficient to extract water present in the crude acetonitrile and the crude acetonitrile is mixed to divide it into an organic liquid phase and an aqueous liquid phase. The formed aqueous liquid phase is removed, and the residual organic liquid phase is subjected to extractive distillation in the presence of 0.5 to 5% by weight of water in a rectifying column. A concentrate of oxazole, in the form of a mixture with water and a small amount of acetonitrile, is separated from the upper part of the column, while acetonitrile free of hydrogen cyanide, allyl alcohol, oxazole or water is recovered from the lower part of the column.

A typical instance of the crude acetonitrile that is purified according to this embodiment is crude acetonitrile obtained in the process for manufacturing acrylonitrile or methacrylonitrile by ammoxidation of propylen or isobutylene. However, other crude acetonitrile can also be purified in this embodiment, provided that the contents of free hydrogen cyanide, cyanohydrin type, hydrogen cyanide, allyl alcohol, oxazole and water are less than 10% by weight, less than 7% by weight, from 5 ppm to 10% by weight, from 100 ppm to 20% by weight and from 5 to 85% by weight, respectively.

This process for the purification of crude acetonitrile containing hydrogen cyanide, allyl alcohol, oxazole and water is based on the following findings in the above processes (v) and (vi).

(1) When an alkali is added to crude acetonitrile in an amount substantially equimolar to the free hydrogen in the crude acetonitrile to effect a reaction and the reaction mixture is subjected to distillation under reduced pressure, removal of hydrogen cyanide and concentration of acetonitrile can be simultaneously accomplished.

(2) When the amount of water present in crude acetonitrile is an amount necessary for formation of an azeotropic mixture with acetonitrile and an azeotropic mixture with allyl alcohol or an amount close to this amount, the relative volatility of acetonitrile to allyl alcohol is remarkably increased.

(3) When an alkali, which is ordinarily considered to cause hydrolysis of acetonitrile very easily, is added under specific conditions, for example, under specific temperature conditions, the crude acetonitrile is effectively purified at a high efficiency by the alkali without hydrolysis of acetonitrile.

(4) When crude acetonitrile is subjected to extractive distillation in the presence of a specific amount of water in a rectifying column, oxazole can surprisingly be separated and removed at a very high efficiency together with other low-boiling-point impurities.

The kind and amount of the alkali used for converting free hydrogen cyanide to an alkali cyanide and the alkali treatment conditions may be the same as described as in (i) above. The amount of water made present in the crude acetonitrile which has been subjected to the alkali treatment and the conditions for reduced pressure distillation in the rectifying column may be the same as described in (i) above.

After hydrogen cyanide and allyl alcohol have been separated and removed from the crude acetonitrile by the reduced pressure distillation in the presence of water, the residual crude acetonitrile is divided into an aqueous liquid phase and an organic liquid phase by extracting water with an alkali. The aqueous layer is removed, and the organic liquid phase is subjected to extractive distillation in the presence of water in a rectifying column in the same manner as described above with respect to the process (iv).

Typical operation procedures for purifying crude acetonitrile will be illustrated with reference to the accompanying drawings.

Referring to FIG. 1 illustrating a flow sheet of the process for separating hydrogen cyanide from crude acetonitrile containing hydrogen cyanide, the crude acetonitrile and an aqueous alkali solution are fed by way of lines 2 and 3, respectively, to a mixing reaction vessel 1 where the mixture is heated by steam supplied by way of line 4 and stirred by a stirring means 5. The reaction mixture, withdrawn from the mixing reaction vessel 1, is continuously introduced by way of line 6 into a rectifying column 7 having, for example, perforated plate trays. The inlet of the reaction mixture may be provided, for example, at a height corresponding to about one tenth of the column height from the bottom. The rectifying column 7 is maintained at a reduced pressure of from 50 to 400 Torr. The column bottom temperature is maintained at 30° to 70° C. by steam supplied by way of line 12 to the bottom of the column. A gaseous azeotropic mixture of acetonitrile and water are withdrawn from the top 8 of the column, and water is withdrawn from the bottom 9 of the column. A portion of the azeotropic mixture, liquefied and collected in a reflux reservoir 31, is returned as reflux through line 10 to the rectifying column, and the remaining portion is recovered through line 11 as purified acetonitrile. A portion of the water from the column bottom is converted to steam by an evaporator 45 and supplied through line 12 to the bottom of the column, and the remaining portion is drained off through line 13 as waste water containing alkali cyanide and cyanohydrin type hydrogen cyanide.

The advantages of the above-mentioned process for the removal of hydrogen cyanide and summarized as follows. Hydrogen cyanide can be substantially completely removed from crude acetonitrile by using a small amount of an alkali and without the use of special chemicals. A concentrated acetonitrile can be recovered at an enhanced yield. The decomposition of acetonitrile can be avoided because an excessive amount of an alkali is not used and the purification operation is carried out at a low temperature. In general, when crude acetonitrile containing 0.1 to 10% by weight of hydrogen cyanide is treated by the above-mentioned process, the removal percent of hydrogen cyanide is at least 99% and the recovery ratio of acetonitrile is at least 98%.

Figure 2:
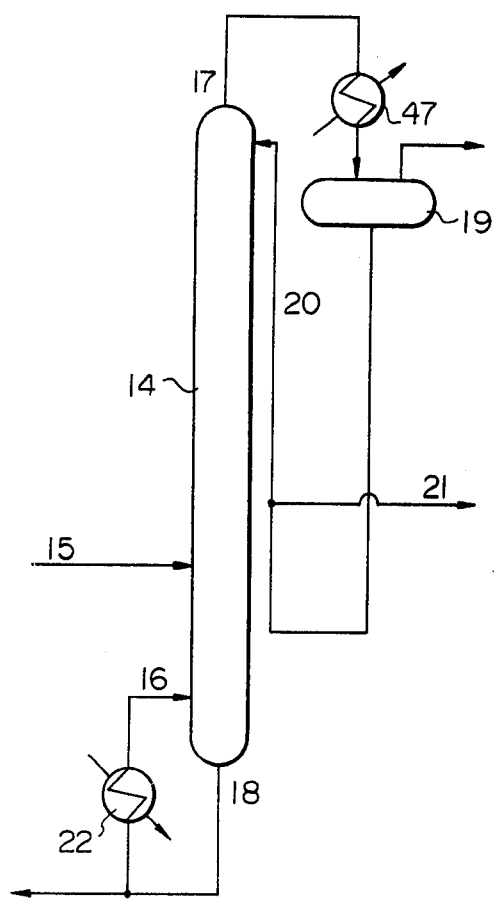
FIG. 2 is a flow sheet illustrating one embodiment of the process for separating allyl alcohol from crude acetonitrile containing allyl alcohol.

Referring to FIG. 2 illustrating a flow sheet of the process for removing allyl alcohol from crude acetonitrile containing allyl alcohol, the crude acetonitrile is introduced into a medial part of a rectifying column 14 by way of line 15. The number of trays in the rectifying column is not particularly limited provided that the number of trays is at least 10. However, a preferable number of trays is in the range of from 20 to 60. The bottom of the column is maintained at a temperature of from 30° to 95° C., preferably from 40° to 60° C. by steam supplied by way of line 16. Vacuum distillation is carried out at a column top temperature of from 20° to 80° C., preferably from 30° to 50° C. and a pressure of from 50 to 760 Torr, preferably 80 to 400 Torr, more preferably from 100 to 200 Torr. Thus, a distillate comprised of acetonitrile and water issues from the top 17 of the column. The distillate is cooled and a portion of the distillate is returned as a reflux through a reflux vessel 19 and by way of line 20 to the column 14. The remaining portion of the distillate is recovered as purified acetonitrile from the reflux reservoir 19 through line 21. A mixture comprised of water, allyl alcohol and a small amount of acetonitrile issues from the bottom 18 of the column, and a portion of the mixture is converted to steam by an evaporator 22 and supplied to the bottom of the column through line 16. The remaining portion of the mixture is drained off.

Thus, allyl alcohol in the crude acetonitrile can be substantially completely removed, and hence, acetonitrile can be recovered steadily at a recovery of from 96 to 97.5% or more. It is advantageous that the mixture issuing from the bottom of the column contains from 1 to 5% by weight of acetonitrile. When the acetonitrile concentration is in this range, the desired recovery of acetonitrile and the substantially complete removal of allyl alcohol can be attained.

Figure 3:
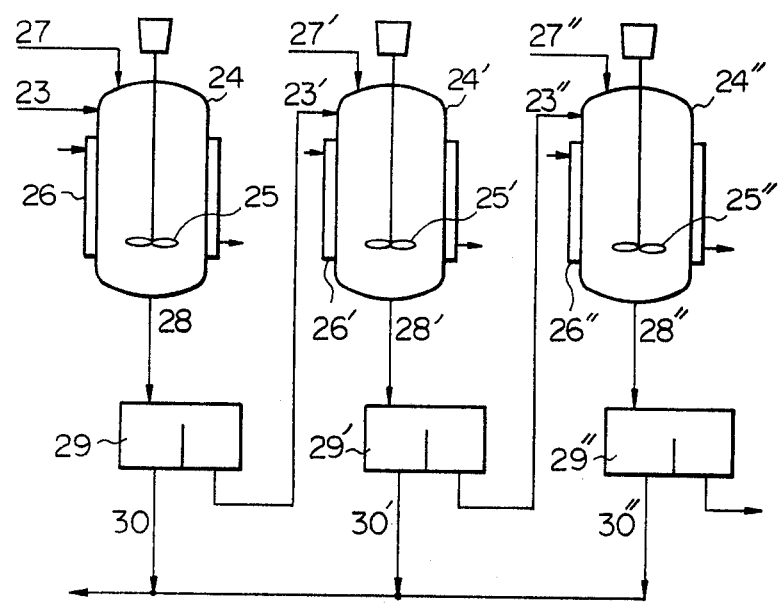
FIG. 3 is a flow sheet illustrating one embodiment of the process for separating water from crude aqueous acetonitrile.

Referring to FIG. 3 illustrating a flow sheet of a process for removing water from crude acetonitrile containing water, crude acetonitrile and a concentrated aqueous alkali solution are introduced into a first extraction vessel 24 by way of line 23 and line 27, respectively. The mixture of the crude acetonitrile and the alkali solution is stirred by a stirring means 25 for about 5 minutes. Since this reaction is exothermic, the mixture is cooled and maintained at a temperature of from 10° to 50° C., preferably from 20° to 30° C. by a temperature controlling means 26. Then, the mixture is transferred from the extraction vessel through line 28 to a first separator 29 where the mixture is divided into an organic liquid phase and an aqueous liquid phase. The organic liquid phase is introduced into a second extraction vessel 24' by way of line 23'. The aqueous liquid phase is collected through line 30.

In the second extraction vessel 24', the organic liquid phase is mixed with a concentrated aqueous alkali solution supplied by way of line 27'. The mixture is stirred by a stirring means 25' and its temperature is controlled by a temperature controlling means 26', in a manner similar to that mentioned with reference to the first extraction vessel 24. Then, the mixture is transferred through line 28' to a second separator 29' where the mixture is divided into an organic liquid phase and an aqueous liquid phase. The aqueous liquid phase is collected through line 30'. The organic liquid phase is introduced by way of line 23" into a third extraction vessel 24" provided with a stirring means 25" and a temperature controlling means 26". In the third extraction vessel 24", the organic liquid phase is treated with alkali supplied by way of line 27" in a manner similar to those mentioned with reference to the first and second extraction vessels. The mixture is then withdrawn from the third extraction vessel 24" through line 28" and divided into an organic liquid phase and an aqueous liquid phase in a third separator 29'''. The aqueous liquid phase is withdrawn through line 30'' and collected together with the aqueous liquid phase from the first and second separators 29 and 29'. The collected solution can be reused, if desired, after being conentrated as an alkali source for the purification of crude acetonitrile. The organic liquid phase is recovered as purified acetonitrile.

Although the above-mentioned dehydration process is directed to a three stage extraction-separation procedure, the dehydration may be effected either in a single stage or in a multi-stage rather than the three stage. The number of stages and the amounts of an alkali used in the respective stages are readily determined from the mutual solubilities of acetonitrile, the alkali and water. It now has been found that, even when crude acetonitrile contains impurities in addition to water, such as hydrogen cyanide and acrylonitrile, such impurities impart little or no influence to the dehydration efficiency.

Instead of using the above-mentioned extraction vessels and separators, a countercurrent extraction column may be used. The countercurrent extraction column is advantageously employed for purifying crude acetonitrile containing water in a continuous manner. Referring to FIG. 4 illustrating a countercurrent extraction column, crude acetonitrile having a specific gravity less than that of an aqueous alkali solution is introduced by way of line 33 into a lower part of the extraction column 32, and concurrently therewith, a concentrated aqueous alkali solution is introduced by way of line 34 into an upper part of the extraction column 32. In the extraction column 32, the crude acetonitrile is countercurrently contacted with the concentrated aqueous alkali solution to be thereby dehydrated. The dehydrated acetonitrile is withdrawn from the top of the extraction column 32 through line 35. The aqueous alkali solution, diluted with the extracted water, is withdrawn from the bottom of the extraction column 32 through line 36. As the extraction column used, a conventional spray type column is conveniently used.

Referring to FIG. 5 illustrating a flow sheet of the process for removing oxazole from crude acetonitrile containing oxazole, the crude acetonitrile is continuously introduced by way of line 38 into a distillation column 37 having sieve trays. An inlet for the crude acetonitrile is provided at a height corresponding to two thirds of the column height from the bottom. Steam is introduced by way of line 40 so that the column bottom temperature is maintained at 85° to 90° C., preferably at 87° to 89° C. and the column top temperature is maintained at 75° to 80° C. Purified acetonitrile is withdrawn from the lower part of the column 37 through line 39. A liquid containing oxazole and other low boiling point impurities is withdrawn from the upper part of the column 37 through line 41 and introduced into a reflux reservoir 42. A portion of the liquid from the reflux reservoir 42 is returned as a reflux to the column 37 through line 43 and the remaining portion of the liquid is discharged through line 44.

By the above-mentioned continuous operation, purified acetonitrile can be obtained at a high recovery ratio. For example, when the crude acetonitrile containing 1.0 to 2.0% by weight of oxazole is purified, the content of oxazole can be reduced to a trace, i.e., 30 ppm of less, and the recovery ratio of acetonitrile can be 93 to 95%. Although the recovery ratio of acetonitrile is at such a level, the content of water can be reduced to 200–500 ppm.

The removal of hydrogen cyanide and allyl alcohol from crude acetonitrile containing hydrogen cyanide and allyl alcohol can be effected by using an apparatus similar to that illustrated in FIG. 1. Referring to FIG. 1, the crude acetonitrile and an aqueous alkali solution are introduced by way of lines 2 and 3, respectively, to a mixing reaction vessel 1 where the mixture is heated to a temperature of from 20° to 80° C. for 0.5 to 10 hours by steam supplied by way of line 4 while the mixture is stirred by a stirring means 5. Thereafter, the reaction mixture is withdrawn from the mixing reaction vessel 1 and continuously introduced by way of line 6 into a rectifying column 7. The rectifying column 7 has, for example, perforated plate trays, and is provided with an inlet for the introduction of the reaction mixture at a height corresponding to about one tenth of the column height from the bottom. The column pressure is maintained at 50 to 400 Torr by a vacuum means (not shown in FIG. 1). The column bottom temperature is maintained preferably at 30° to 70° C. by steam supplied from an evaporator 45 by way of line 12 into the lower part of the column. The column top temperature reaches about 30° to 50° C. A gaseous azeotropic mixture of acetonitrile and water are withdrawn from the top of the column 7 through line 8, liquefied by a cooler 46 and collected in a reflux reservoir 31. A portion of the liquid mixture is returned as reflux through line 10 to the rectifying column 7, and the remaining portion is collected through line 11 as purified acetonitrile from which allyl alcohol and hydrogen cyanide have been removed. A portion of the liquid issuing from the bottom of the column 7 is introduced through line 9 into the evaporator 45 and the remaining portion is drained off through line 13. The liquid issuing from the bottom of the column 7 is comprised of allyl alcohol, alkali cyanide, cyanohydrin-type hydrogen cyanide, acetonitrile and water.

The removal of water and oxazole from crude acetonitrile containing water and oxazole can be effected by using an apparatus which is a combination of the apparatus illustrated in FIG. 3 or 4 with the apparatus illustrated in FIG. 5. For example, the crude acetonitrile containing water and oxazole is continuously introduced by way of line 33 into a counter current extraction column 32 as illustrated in FIG. 4. Concurrently therewith, a concentrated aqueous alkali solution is introduced by way of line 34 into the extraction column 32. The extraction column has, for example, a height of 8 m in which ½ inch iron Raschig rings are packed along a height of 6 m. In the extraction column 32, the crude acetonitrile is countercurrently contacted with the concentrated aqueous alkali solution to be thereby dehydrated. The dehydrated acetonitrile is withdrawn from the top of the extraction column 32 through line 35. The aqueous alkali solution, diluted with the extracted water, is withdrawn from the bottom of the extraction column 32 through line 36.

The dehydrated acetonitrile is transferred to a distillution apparatus similar to that illustrated in FIG. 5, wherein the dehydrated acetonitrile is distilled. That is, referring to FIG. 5, the acetonitrile is continuously introduced by way of line 38 into a distillation column 37 having sieve trays. An inlet for the crude acetonitrile is provided at a height corresponding to two thirds of the column height from the bottom. Steam is introduced from an evaporator 49 by way of line 40 so that the column bottom temperature is maintained at 85° to 90° C. The column top temperature reaches 70° to 80° C. Purified acetonitrile is withdrawn from the bottom of the column 37 through line 39. A gaseous mixture containing oxazole, water, acetonitrile and other low boiling point impurities is withdrawn from the top of the column 37 through line 41, liquefied by a cooling means 48 and introduced into a reflux reservoir 42. A portion of the liquid from the reflux reservoir 42 is returned as a reflux to the column 37 through line 43 and the remaining portion of the liquid is discharged through line 44.

Figure 6:
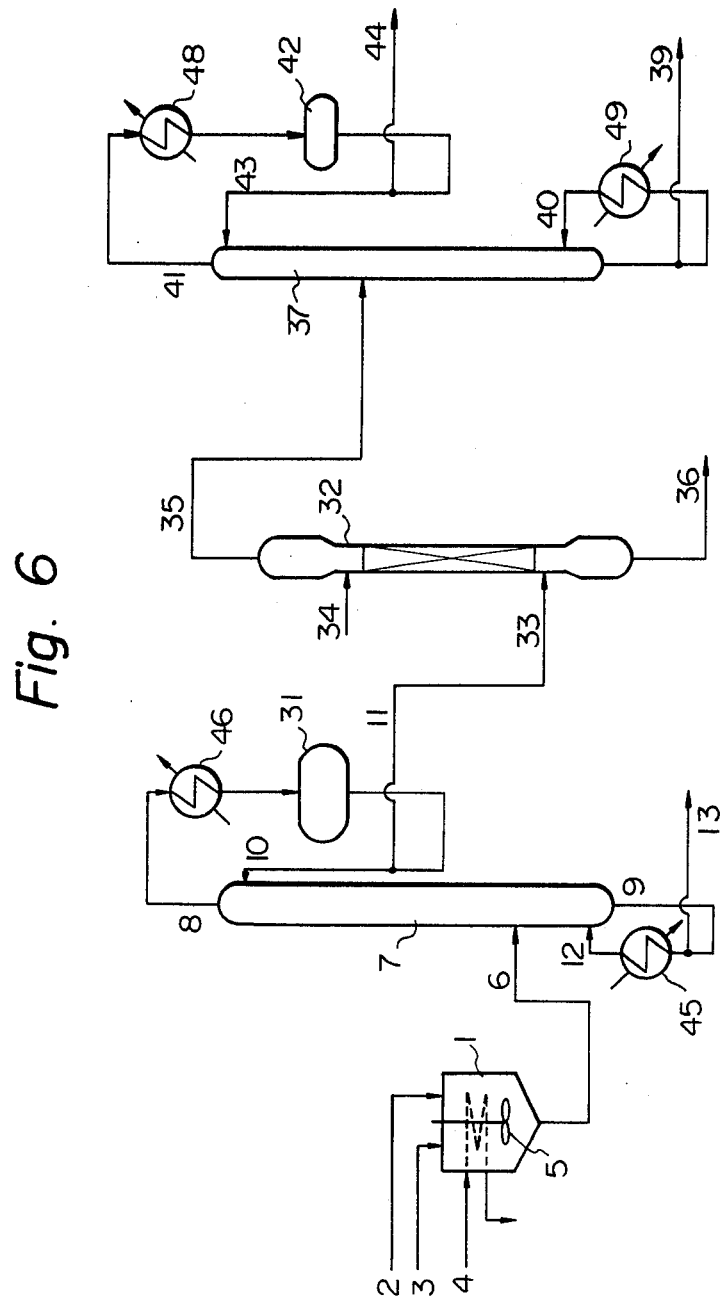

Referring to FIG. 6 illustrating a flow sheet of the process for removing hydrogen cyanide, allyl alcohol, water and oxazole from crude acetonitrile containing these impurities, the entire apparatus is a combination of the apparatus illustrated in FIGS. 1, 4 and 5. The crude acetonitrile and an aqueous alkali solution are fed by way of lines 2 and 3, respectively, to a mixing reaction vessel 1 where the mixture is heated by steam supplied by way of line 4 and stirred by a stirring means 5. The reaction mixture is maintained at a temperature of from 20° to 80° C. for about 0.5 to 10 hours, and then, withdrawn from the mixing reaction vessel 1. The mixture is then continuously introduced by way of line 6 into a rectifying column 7 having, for example, perforated plate trays. The inlet of the reaction mixture may be provided, for example, at a height corresponding to about one tenth of the column height from the bottom. The rectifying column 7 is maintained at a reduced pressure of from 50 to 400 Torr by a vacuum means (not shown in FIG. 6). The column bottom temperature is maintained preferably at 30° to 70° C. by steam supplied from an evaporator 45 by way of line 12 to the lower part of the column. The column top temperature reaches about 30° to 50° C. A gaseous mixture comprised of an azeotrope of acetonitrile with water and oxyazole is withdrawn from the top of the column through line 8, liquefied by a cooling means 46 and collected in a reflux reservoir 31. A portion of the liquid in the reservoir 31 is returned as reflux through line 10 to the rectifying column 7, and the remaining portion is transferred through line 11 to the succeeding dehydration step. A portion of the liquid withdrawn from the column bottom is converted to steam by the evaporator 45 and supplied to the lower part of the column through line 12, and the remaining portion is drained off through line 13 as waste water containing alkali cyanide, cyanohydrin type hydrogen cyanide, allyl alcohol and acetonitrile.

The liquid comprised of acetonitrile, oxazole and water and transferred through line 11 is introduced by way of line 33 into a lower part of an extraction column 32, and concurrently therewith, a concentrated aqueous alkali solution is introduced by way of line 34 into an upper part of the column 32. The column 32 has, for example, a height of 8 m, in which ½ inch iron Raschig rings are packed along a height of 6 m. In the extraction column 32, the acetonitrile-containing liquid is countercurrently contacted with the aqueous alkali solution to be thereby dehydrated. Thus, the content of water in the liquid is reduced to an extent such that the dehydrated liquid can be effectively treated in the succeeding step of removing oxazole therefrom. The dehydrated liquid, i.e., acetonitrile is withdrawn from the top of the column 32 through line 35. The aqueous alkali solution, diluted with the extracted water, is withdrawn as an aqueous liquid phase from the bottom of the column 32 through line 36.

The acetonitrile containing oxazole withdrawn through line 35 is introduced into a distillation column 37 having sieve trays. An inlet for the acetonitrile is provided at a height corresponding to two thirds of the column height from the bottom. Steam is introduced from an evaporator 49 by way of line 40 so that the column bottom temperature is maintained at 85° to 90° C. The column top temperature reaches 70° to 80° C. A gaseous mixture containing oxazole, water and other low boiling point impurities is withdrawn from the top of the column 37 through line 41, liquefied by a cooling means 48 and introduced into a reflux reservoir 42. A portion of the liquid from the reflux reservoir 42 is returned as reflux to the column 37 through line 43 and the remaining portion of the liquid is discharged through line 44. Purified acetonitrile is withdrawn from the bottom of the column 37 through line 39, while a portion thereof is circulated through the evaporator 49 and line 40 into the column 37.

The present invention will now be described in detail with reference to the following Examples that by no means limit the scope of the invention. In these Examples, "%" is by weight unless otherwise indicated.

EXAMPLE 1

A 25% aqueous sodium hydroxide solution was incorporated in 600 g of crude acetonitrile containing 0.3% free hydrogen cyanide, 0.7% cyanohydrin type hydrogen cyanide and 29% water in a mixing reaction vessel. The amount of sodium hydroxide used was equimolar to the free hydrogen cyanide contained in the crude acetonitrile. The liquid mixture was stirred for 5 hours at 70° C. and was then fed at a rate of 600 g/hr to a perforated plate rectifying column having 50 plates each possessing a diameter of 25 mm. In this rectifying column, the column bottom pressure was maintained at 150 Torr, and the column bottom temperature was maintained at 53° C.

Acetonitrile having a concentration of 88.5% was recovered at a rate of 465 g/hr from the top of the column. The hydrogen cyanide content in the recovered purified acetonitrile was 8 ppm, and the acetonitrile recovery ratio was 98%.

EXAMPLE 2

To crude acetonitrile containing 0.3% free hydrogen cyanide, 0.7% cyanohydrin type hydrogen cyanide and 29.1% water was added an aqueous solution containing sodium hydroxide, the sodium hydroxide being in an amount of 2 mols per mol of the free hydrogen cyanide, and the liquid mixture was treated in the same manner as described in Example 1. Purified acetonitrile having the composition indicated below was recovered at a rate of 465 g/hr.

| Component | Content |
| --- | --- |
| Total hydrogen cyanide | 6 ppm |
| Water | 11.0% |
| Acetonitrile | 88.9% |

EXAMPLE 3

To 550 g of crude acetonitrile containing 0.2% free hydrogen cyanide, 0.5% cyanohydrin type hydrogen cyanide and 30% water was added 3.05 g of a 50% aqueous solution of sodium hydroxide (the amount of sodium hydroxide being substantially equimolar to the free hydrogen cyanide), and the mixture was stirred under atmospheric pressure at 20° C. for 10 hours. The reaction mixture was fed to the same column described in Example 1, and vacuum distillation was carried out at a column bottom temperature of 53° C. under a pressure of 150 Torr.

The initial fraction (414 g) from the top of the column was found to have the following composition.

| Component | Content |
|---|---|
| Total hydrogen cyanide | 12 ppm |
| Water | 10% |
| Acetonitrile | 89.9% |

Comparative Example 1

The treatment was conducted in the same manner as described in Example 3 except that the amount of the 50% aqueous solution of sodium hydroxide was changed to 1.62 g (the amount of sodium hydroxide being 0.5 mol per mol of the free hydrogen cyanide in the crude acetonitrile). The initial fraction (417 g) from the packed column was found to have the following composition.

| Component | Content |
|---|---|
| Total hydrogen cyanide | 1200 ppm |
| Water | 10.1% |
| Acetonitrile | 89.8% |

EXAMPLE 4

A 25% aqueous solution of sodium hydroxide was added to crude acetonitrile containing 70% acetonitrile, 29% water, 0.7% cyanohydrin type hydrogen cyanide and 0.3% free hydrogen cyanide (the amount of sodium hydroxide being equimolar to the free hydrogen cyanide in the crude acetonitrile), and the mixture was stirred for 5 hours at 70° C. Thereafter, the mixture was treated in the same rectifying column as used in Example 1 under the operation conditions shown in Table 1, below. The composition of each distillate is also shown in Table 1, below.

indicated below was recovered from the top of the column at a rate of 438 g/hr.

| Component | Content (%) |
|---|---|
| Acetonitrile | 89.2 |
| Water | 9.2 |
| Allyl alcohol | Trace |
| Other impurities | 1.6 |

EXAMPLE 6

The same crude acetonitrile as used in Example 5 was treated in the same apparatus as used in Example 5 under a column bottom pressure of 450 Torr, a column bottom temperature of 65° C., and a reflux ratio of 2.7.

Acetonitrile having the composition indicated below was recovered from the top of the column at a rate of 452 g/hr.

| Component | Content (%) |
|---|---|
| Acetonitrile | 85.8 |
| Water | 12.6 |
| Allyl alcohol | trace |
| Other impurities | 1.6 |

EXAMPLE 7

An apparatus similar to that illustrated in FIG. 3 was used.

A 4000 liter volume extraction vessel provided with a stirrer and a cooling coil was charged with 3370 kg of crude acetonitrile containing 28.0% water, 70.0% acetonitrile, 1.9% hydrogen cyanide and 0.1% other impurities. 105 kg of a 50% aqueous solution of sodium hydroxide were added to the charge under agitation over a period of 2 minutes while maintaining the charge at 30° C. by passing cooling water through the cooling coil. Subsequently, the mixture was stirred for 3 minutes and then transferred to a separation tank to perform a separation treatment. There were obtained an organic liquid phase consisting of 2863 kg of crude aqueous acetonitrile comprised of 20.4% water, 78.3% acetonitrile and 1.3% other impurities and an aqueous liquid phase consisting of 612 kg of a dilute sodium hydroxide solution comprised of 8.6% sodium hydroxide, 19.0%

TABLE I

| | Operation Conditions | | | | Distillate | | | | |
|---|---|---|---|---|---|---|---|---|---|
| Run No. | Amount Charged (g) | NaOH/F—CN Molar Ratio | Pressure (Torr) | Temperature (°C.) | Acetonitrile (%) | Water (%) | Hydrogen Cyanide (ppm) | Total Amount (g) of Distillate | Hydrogen Cyanide Removal Percent (%) |
| 1 | 600 | 1.0 | 150 | 53 | 90.5 | 8.5 | trace | 455 | 99.99 |
| 2 | 600 | 1.0 | 155 | 54 | 90.2 | 8.9 | 2.58 | 458 | 99.98 |
| 3 | 600 | 1.0 | 300 | 59 | 89.9 | 9.8 | 6.6 | 459 | 99.95 |
| 4 | 600 | 1.0 | 310 | 60 | 87.5 | 12.3 | 8.3 | 471 | 99.93 |

EXAMPLE 5

An apparatus similar to that illustrated in FIG. 2 was used. A perforated plate column having 50 plates was used as the rectifying column 1. Crude acetonitrile containing 31.2% water, 0.6% allyl alcohol and 1.5% other impurities was fed at a rate of 600 g/hr to the 5th plate of the rectifying column, and the crude acetonitrile was distilled under a column bottom pressure of 180 Torr, a column bottom temperature of 55° C. and a reflux ratio of 2.7. Purified acetonitrile having the composition acetonitrile, 67.4% water and 5.0% other impurities.

The so obtained crude aqueous acetonitrile was charged into the extraction vessel again and treated in the same manner as described above. Thus, the treatment was similarly repeated 3 times. Compositions of the organic liquid phase and aqueous liquid phase obtained at each treatment are shown in Table II, below.

TABLE II

| Products | Second Extraction | Third Extraction | Fourth Extraction |
|---|---|---|---|
| Organic Liquid Phase | | | |
| Water (%) | 10.2 | 4.7 | 3.2 |
| Acetonitrile (%) | 89.3 | 95.1 | 96.6 |
| Other impurities (%) | 0.5 | 0.2 | 0.2 |
| Weight (kg) | 2449 | 2281 | 2236 |
| Aqueous Liquid Phase | | | |
| Acetonitrile (%) | 10.6 | 6.4 | 4.4 |
| Water (%) | 74.5 | 71.5 | 56.5 |
| Sodium hydroxide (%) | 10.1 | 19.2 | 33.5 |
| Other impurities (%) | 4.8 | 2.8 | 5.5 |
| Weight (kg) | 519 | 273 | 156 |

EXAMPLE 8

Crude acetonitrile containing 20% water and a 52% aqueous solution of sodium hydroxide were fed to a countercurrent extraction column having a structure similar to that illustrated in FIG. 4 and a height of 8 m, in which ½ inch iron Raschig rings were packed along a height of 6 m. The purifying treatment was carried out to obtain the results shown in Table III, below.

TABLE III

| Component | Crude Acetonitrile | Concentrated Sodium Hydroxide Solution | Purified Acetonitrile | Dilute Sodium Hydroxide Solution |
|---|---|---|---|---|
| Water (%) | 20.0 | 52 | 3.0 | 83.8 |
| Acetonitrile (%) | 80.0 | 0 | 97.0 | 3.0 |
| Sodium Hydroxide (%) | — | 48 | — | 13.2 |
| Amount (kg/hr) | 450 | 31 | 368 | 113 |

EXAMPLE 9

A 300 liter volume extraction vessel equipped with a stirrer was charged with 200 liters of crude acetonitrile, and 8 liters of a 50% aqueous solution of sodium hydroxide was gradually added to the crude acetonitrile while maintaining the temperature at 30°–40° C. The mixture was vigorously agitated for 3 minutes and was then transferred to a separation tank to divide the mixture into an organic liquid phase and an aqueous liquid phase. The organic liquid phase was returned to the extraction vessel and the aqueous liquid phase was withdrawn. This operation was repeated 3 times. The obtained results are shown in Table IV, below.

TABLE IV

| products | Starting Liquid | First Extraction | Second Extraction | Third Extraction |
|---|---|---|---|---|
| Organic Liquid Phase | | | | |
| Water (%) | 27.1 | 8.2 | 3.2 | 1.5 |
| Acetonitrile (%) | 72.9 | 91.8 | 96.8 | 98.5 |
| Weight (kg) | 165.4 | 131.3 | 124.3 | 120.5 |
| Aqueous Liquid Phase | | | | |
| Water (%) | 50 | 87.0 | 68.2 | 57.6 |
| Sodium hydroxide (%) | 50 | 13.0 | 31.8 | 42.4 |
| Weight (kg) | 12.0 | 46.1 | 18.9 | 15.8 |

EXAMPLE 10

A rectifying column having 40 plates similar to that illustrated in FIG. 5, was used. Crude acetonitrile containing 97.2% acetonitrile, 1.0% water, 0.3% ammonia, 1.5% oxazole and a trace amount of suspended solids was fed at a rate of 600 kg/hr into the column having a feed inlet at the 27th plate and, by steam, the column bottom temperature and column top temperature were maintained at 90° C. and 76° C., respectively. The fractionating operation was carried out at a reflux ratio of 60. A distillate containing 12.1% water, 19.9% oxazole and 64% acetonitrile was withdrawn at a rate of 45.3 kg/hr from the top of the column, and purified acetonitrile was withdrawn at a rate of 554.5 kg/hr through line 39. The purified acetonitrile contained 0.02% water, 2 ppm ammonia and 10 ppm oxazole. The recovery ratio of acetonitrile was 95.0%.

EXAMPLE 11

Following a procedure similar to that mentioned in Example 1, various crude acetonitriles were purified wherein the alkali treatment and fractionating conditions and the compositions of the crude acetonitriles were varied as shown in Table V, below. All other conditions remained substantially the same. The compositions of the resultant distillates are shown in Table V, below.

TABLE V

| Run No. | Amount of charged Crude CH$_3$CN | Alkali Treating and Fractionating Conditions ||||||| Composition*2 |||||| Recovery of CH$_3$CN (%) |
|---|---|---|---|---|---|---|---|---|---|---|---|---|---|---|
| | | NaOH/F—HON Molar Ratio | Alkali Treating Temperature (°C.) | Alkali Treating Time (hour) | Column Bottom Pressure (Torr) | Column Bottom Temperature (°C.) | Amount*1 (g/H) | conc. of CH$_3$CN (%) | HCN*3 | Allyl Alcohol | H$_2$O (%) | other Impurities (%) | |
| 1*4 | 650 | 0.5 | 70 | 6 | 180 | 55 | (650) | (61.2) | (C 2000 ppm) (F 7000 ppm) | (5500 ppm) | (35.0) | (2.35) | 99.1 |
| 2*4 | 632.6 | 0.8 | 70 | 6 | 180 | 55 | 445.43 (632.6) | 88.5 (61.24) | T 1300 ppm (C 2000 ppm) (F 7000 ppm) | 14 ppm (6000 ppm) | 9.07 (35.0) | 2.30 (2.26) | 99.5 |
| 3 | 600 | 1.0 | 70 | 6 | 180 | 55 | 434.34 (600) | 88.75 (58.10) | T 400 ppm (C 3000 ppm) (F 8000 ppm) | 35 ppm (5500 ppm) | 9.0 (38.0) | 2.21 (2.25) | 98.00 |
| 4 | 624.5 | 1.1 | 70 | 6 | 180 | 55 | 384.4 (624.5) | 88.86 (61.2) | T 6.7 ppm (C 2000 ppm) (F 7000 ppm) | 12 ppm (6000 ppm) | 8.71 (35.0) | 2.43 (2.3) | 98.50 |
| 5 | 650 | 2.0 | 75 | 6 | 180 | 55 | 423.7 (650) | 88.86 (61.2) | T 7.4 ppm (C 2.0%) (F 7.0%) | 30 ppm (5500 ppm) | 8.92 (35.0) | 2.22 (2.35) | 93.0 |
| 6 | 630 | 2.5 | 75 | 6 | 180 | 55 | 418.1 (630) | 83.47 (61.2) | T 4.54 ppm (C 1.3%) (F 3.2%) | 88 ppm (5500 ppm) | 9.09 (35.0) | 2.44 (2.35) | 94.98 |
| 7 | 650 | 1.0 | 25 | 0.5 | 220 | 58 | 414.8 (650) | 88.03 (72.3) | T 3.26 ppm (C 2.3%) (F 4.0%) | 53 ppm (150 ppm) | 9.44 (18.88) | 2.53 (2.52) | 98.0 |
| 8 | 650 | 2.0 | 25 | 1.0 | 220 | 58 | 561 (650) | 82.0 (43.4) | T 25 ppm (C 1.5%) (F 4.3%) | 20 ppm (1200 ppm) | 14.3 (49.14) | 2.32 (1.54) | 98.5 |
| 9 | 650 | 1.05 | 35 | 0.5 | 220 | 58 | 339 (650) | 82.0 (58.3) | T 19 ppm (C 0.2%) (F 0.7%) | 30 ppm (2.5%) | 15.4 (36.1) | 2.3 (2.2) | 96.8 |
| 10 | 650 | 2.0 | 35 | 1.0 | 220 | 58 | 447 (650) | 82.0 (40.2) | T 8 ppm (C 0.4%) (F 1.5%) | 45 ppm (4.0%) | 14.8 (52.69) | 2.52 (1.21) | 94.5 |
| | | | | | | | 301 | 82.0 | T 5.5 ppm | 34 ppm | 15.5 | 2.02 | |

*1 Numerals within parentheses and not within parentheses signify amounts of crude acetonitrile and amounts of distillates, respectively.
*2 Numerals within parentheses and not within parentheses signify compositions of crude acetonitrile and compositions of distillates, respectively.
*3 C: Cyanohydrin-type HCN, F: Free HCN, T: Total of cyanohydrin-type HCN and free HCN.
*4 Comparative Example

EXAMPLE 12

A countercurrent extraction column having a structure similar to that illustrated in FIG. 4 and arranged in a manner similar to that illustrated in the right hand half of FIG. 6 was used. The extraction column had a height of 8 m, in which iron Rasching rings were packed to a height of 6 m. Crude acetonitrile and a concentrated aqueous sodium hydroxide solution were fed into the extraction column at the lower and upper parts thereof, respectively, whereby the crude acetonitrile and the aqueous sodium hydroxide solution were countercurrently contacted with each other in order to transfer a substantial part of the water contained in the crude acetonitrile to the aqueous sodium hydroxide solution. The so formed dilute aqueous sodium hydroxide solution was withdrawn from the bottom of the extraction column. Dehydrated crude acetonitrile was withdrawn from the top of the extraction column, and introduced into a rectifying column as shown in FIG. 5. The rectification was effected by a procedure similar to that mentioned in Example 10.

The water extraction and rectification conditions and the compositions and amounts of (i) crude acetonitrile, (ii) dehydrated crude acetonitrile and (iii) purified acetonitrile are shown in Table VI, below.

each possessing a diameter of 750 mm. In this rectifying column, the column bottom pressure was maintained at 180 Torr and the column bottom temperature was maintained at 55° C. A mixture of sodium cyanide, allyl alcohol and water was withdrawn from the bottom of the rectifying column. Partially purified acetonitrile containing 2.25% oxazole, 9.05% water, 10 ppm hydrogen cyanide and 0.22% low boiling point matters was withdrawn from the top of the rectifying column at a rate of 398.8 kg/hr.

The partially purified acetonitrile was fed at a rate of 398.8 kg/hr to the lower part of a countercurrent extraction column having a height of 8 m, in which ½ inch iron Raschig rings were packed to a height of 6 m. Concurrently therewith, a 50% aqueous sodium hydroxide solution was fed at a rate of 22 kg/hr to the upper part of the extraction column. Both the partially purified acetonitrile and the 50% aqueous sodium hydroxide solution were maintained at 30° C. Partially purified and dehydrated acetonitrile containing 2.47% oxazole, 1.49% water and 0.25% other impurities was withdrawn at a rate of 364.59 kg/hr from the top of the extraction column. An aqueous sodium hydroxide solution, diluted with the water extracted from the partially purified acetonitrile, was withdrawn at a rate of 53.37 kg/hr from the bottom of the extraction column. A part

TABLE VI

| | Water Extracting Conditions | | | | | | Distillating Conditions | | | | | |
|---|---|---|---|---|---|---|---|---|---|---|---|---|
| | Amount of 50% | | | Column | | | | Composition | | | | |
| Run No. | NaOH (in terms of pure NaOH) (kg/H) | Temperature (°C.) | Column Bottom Pressure (kg/cm²) | Bottom Temperature (°C.) | R/D | *1 | Flow Rate (kg/H) | CH₃CN (%) | Oxazole (ppm) | Water (%) | Other Impurities (%) | Recovery of Acetonitrile (%) |
| 1 | 6.5 | 20 | 0.1 | 88 | 25 | A | 393.9 | 88.6 | 23000 | 8.30 | 0.8 | 99 |
| | | | | | | B | 363.18 | 95.18 | 24500 | 1.48 | 0.88 | 98.3 |
| | | | | | | C | 339.8 | 99.9 | 10 | 150 ppm | 0 | |
| 2 | 6.09 | 20 | 0.1 | 87.8 | 25 | A | 468.89 | 88.55 | 24100 | 8.66 | 0.38 | 99 |
| | | | | | | B | 430.17 | 95.54 | 26200 | 1.42 | 0.42 | 94.3 |
| | | | | | | C | 391.5 | 99.9 | 15 | 250 ppm | 0 | |
| 3 | 5.19 | 20 | 0.1 | 87.9 | 24.5 | A | 406.85 | 88.54 | 22100 | 8.5 | 0.74 | 99 |
| | | | | | | B | 373.42 | 95.50 | 24100 | 1.48 | 0.62 | 94.10 |
| | | | | | | C | 335.63 | 99.9 | 30 | 280 ppm | 0 | |
| 4 | 33.75 | 20 | 0.1 | 88 | 25 | A | 500 | 50.0 | 22300 | 45.0 | 2.77 | 99 |
| | | | | | | B | 258.7 | 94.7 | 43000 | 1.0 | 0 | 95.5 |
| | | | | | | C | 238.8 | 99.9 | 15 | 80 ppm | 0 | |
| 5 | 60.0 | 20 | 0.1 | 88 | 25 | A | 500 | 15.0 | 3800 | 81.85 | 2.77 | 99 |
| | | | | | | B | 100.13 | 74.15 | 19000 | 2.40 | 13.23 | 93.3 |
| | | | | | | C | 66.99 | 99.9 | 10 | 185 ppm | 0 | |
| 6 | 6.58 | 30 | 0.1 | 88 | 25 | A | 397.9 | 88.7 | 23000 | 8.2 | 0.8 | 99 |
| | | | | | | B | 366.89 | 95.2 | 24500 | 1.47 | 0.87 | 97.8 |
| | | | | | | C | 341.66 | 99.9 | 10 | 200 ppm | 0 | |
| 7 | 4.78 | 30 | 0.1 | 88 | 25 | A | 400 | 88.7 | 22000 | 7.97 | 1.12 | 99 |
| | | | | | | B | 370.02 | 94.87 | 24300 | 1.48 | 1.22 | 98.5 |
| | | | | | | C | 345.85 | 99.9 | 5 | 130 ppm | 0 | |
| 8 | 35.0 | 30 | 0.1 | 88 | 25 | A | 500 | 60.0 | 15000 | 35.73 | 2.76 | 99 |
| | | | | | | B | 326.32 | 91.01 | 23000 | 2.60 | 4.09 | 97.3 |
| | | | | | | C | 292 | 99.9 | 18 | 280 ppm | 0 | |

*1 A: Crude acetonitrile, B: Dehydrated crude acetonitrile, C: Purified acetonitrile.

EXAMPLE 13

A mixing reaction vessel was charged with about 600 kg of crude acetonitrile containing 35% water, 0.7% free hydrogen cyanide, 0.2% cyanohydrin type hydrogen cyanide, 0.6% allyl alcohol, 1.5% oxazole, 0.1% acrylonitrile and 0.65% other impurities. To the charged crude acetonitrile was added a 25% aqueous solution of sodium hydroxide, the amount of sodium hydroxide being equimolar to the free hydrogen cyanide contained in the crude acetonitrile. The liquid mixture was stirred for 6 hours at 75° C.

Then, the mixture was fed at a rate of 624.8 kg/hr to the 5th plate of a rectifying column having 50 plates of the diluted aqueous sodium hydroxide solution was returned to the mixing reaction vessel to remove hydrogen cyanide and allyl alcohol from the crude acetonitrile.

The partially purified and dehydrated acetonitrile, withdrawn from the top of the extraction column, was fed at a rate of 364.59 kg/hr into a rectifying column having 40 plates through a feed inlet provided at the 27th plate thereof. The column bottom temperature and the column top temperature were maintained by steam at 88° C. and 76° C., respectively. The rectifying operation was carried out at a reflux ratio of 25. An acetonitrile containing 23% water, 39% oxazole and 3.9% other impurities was withdrawn at a rate of 23 kg/hr from the top of the column, and purified acetonitrile having a purity of 99.7% was withdrawn at a rate of 341.6 kg/hr from the bottom of the column. The purified acetonitrile, so recovered from the bottom of the column, contained 200 ppm of water, 10 ppm of allyl alcohol and 15 ppm of oxazole. The recovery ratio of acetonitrile was 92.9%.

EXAMPLE 14

Following a procedure similar to that mentioned in Example 13, crude acetonitrile containing water, hydrogen cyanide, allyl alcohol, oxazole, acrylonitrile and other impurities was purified wherein the treating conditions shown in Table VII, below, were employed. All other conditions remained substantially the same. The compositions of (i) crude acetonitrile, (ii) allyl alcohol- and hydrogen cyanide-removed acetonitrile, (iii) dehydrated acetonitrile and (iv) finally purified acetonitrile are shown in Table VII, below.

TABLE VII

| Run No. | Purifying Condition | | | | *1 | Flow Rate (kg/H) | aceto-nitrile (%) | Hydro-gen Cyanide (ppm) | Acrylo-nitrile (ppm) | Oxazole (ppm) | Water (%) | Other Impu-rities (%) | Allyl Alcohol (ppm) | Recovery of Aceto-nitrile (%) |
| | Alkal Treatment | Allyl alcohol and HCN-removal | Dehy-dration | Oxazole-removal | | | | | | | | | | |
|---|---|---|---|---|---|---|---|---|---|---|---|---|---|---|
| 1 | Temp. 70° C. Time 6 hrs NaOH/F—HCN = 2 | Press. 180 Torr Col. Bottom 55° C. Temp. | Temp. 30° C. | Col. Top 75° C. Temp. Col. Botom 88° C. Temp. Col. Bottom 0.1 kg/cm² Press. Reflux Ratio 25 | A B C D | 600 398.8 364.59 341.59 | 61.25 88.4 95.80 99.9 | 9000 10 0 0 | 1000 0 0 0 | 15000 22500 24700 15 | 35.0 9.05 5.42 200 ppm | 0.65 0.22 0.90 0 | 6000 0 0 10 | — 95.97 99.0 97.7 |
| 2 | Temp. 70° C. Time 6 hrs NaOH/F—HCN = 2 | Press. 180 Torr Col. Bottom 55° C. Temp. | Temp. 20° C. | Col. Top 75° C. Temp. Col. Bottom 88° C. Temp. Col. Bottom 0.1 kg/cm² Press. Reflux Ratio 25 | A B C D | 600 395.4 361.48 339.73 | 61.25 88.29 95.61 99.9 | 9000 0 0 0 | 1000 14 0 0 | 15000 22800 24900 10 | 35.0 9.05 1.49 150 ppm | 0.65 0.38 0.41 0 | 6000 50 0 0 | — 95.0 99.0 98.2 |
| 3 | Temp. 70° C. Time 6 hrs NaOH/F—HCN = 2 | Press. 180 Torr Col. Bottom 55° C. Temp. | Temp. 20° C. | Col. Top 75° C. Temp. Col. Bottom 88° C. Temp. Col. Bottom 0.1 kg/cm² Press. Reflux Ratio 25 | A B C D | 600 468.9 430.7 391.5 | 74.41 88.54 95.54 99.9 | 13300 3.5 0 0 | 2300 105 0 0 | 18800 24000 26200 13 ppm | 20.5 8.66 6.09 150 ppm | 0.8 0.38 1.80 0 | 8500 45 0 0 | — 92.98 99.0 95.16 |

*1 A: Crude acetonitrile, B: Allyl alcohol- and hydrogen cyanide-removed acetonitrile, C: Dehydrated acetonitrile and D: Finally purified acetonitrile.

We claim:

1. A process for purifying crude acetonitrile containing water as a major component, which comprises the steps of:

treating the crude acetonitrile with from 10 to 50% of an alkali based on the weight of the water present in the crude acetonitrile, at a predetermined temperature and for a predetermined time such that no substantial hydrolysis of acetonitrile takes place, sufficient to divide the crude acetonitrile into an organic liquid phase, and then removing the aqueous liquid phase.

2. A process according to claim 1, wherein the crude acetonitrile further contains oxazole as a major impurity component, the residual organic liquid after removal of the aqueous liquid phase being subjected to extractive distillation in the presence of 0.5 to 5% by weight of water in a rectifying column, while a concentrate of oxazole in the form of a mixture with water and a small amount of acetonitrile is separated from the upper part of the column, and acetonitrile is recovered from the lower part of the column.

3. A process according to claim 1 or 2, wherein the alkali is sodium hydroxide or potassium hydroxide.

4. A process according to claim 1 or 2, wherein the extraction of water with the alkali is carried out at a temperature of from 10° to 50° C.

5. A process according to claim 2, wherein the acetonitrile to be subjected to the extractive distillation is introduced into the rectifying column at a height corresponding to approximately $\frac{1}{2}$ to approximately $\frac{3}{4}$ of the column height from the bottom.

6. A process according to claim 2, wherein the acetonitrile to be subjected to the extractive distillation is introduced into the rectifying column at a height corresponding to approximately $\frac{2}{3}$ of the column height from the bottom.

7. A process according to claim 2, wherein the acetonitrile to be introduced into the rectifying column for the extractive distillation contains from 0.5% to 5.0% by weight of water.

* * * * *